(12) United States Patent
Muto et al.

(10) Patent No.: US 6,847,381 B2
(45) Date of Patent: Jan. 25, 2005

(54) DENDROGRAM DISPLAYING METHOD

(75) Inventors: Isamu Muto, Kanagawa (JP); Shigeru Yatsuzuka, Kanagawa (JP); Iwao Yamashita, Kanagawa (JP); Takuro Tamura, Kanagawa (JP)

(73) Assignee: Hitachi Software Engineering Co., Ltd., Kanagawa (JP)

(*) Notice: Subject to any disclaimer, the term of this patent is extended or adjusted under 35 U.S.C. 154(b) by 288 days.

(21) Appl. No.: 10/133,160

(22) Filed: Apr. 26, 2002

(65) Prior Publication Data
US 2002/0186226 A1 Dec. 12, 2002

(30) Foreign Application Priority Data

Jun. 7, 2001 (JP) .................................... 2001-172922

(51) Int. Cl.[7] .............................................. C09G 5/00
(52) U.S. Cl. ......................................................... 345/629
(58) Field of Search ......................................... 345/629

(56) References Cited

PUBLICATIONS

Li, Shuying, Pearl, Dennis K., and Doss, Hani. "Phylogenetic Tree Construction using Markov Chain monte Carlo", Revised Nov. 1999.*

Maciukenas, M., "TREETOOL User Manual", Copyright© 1992, 1993, 1994.*

Nadeau, Dave, "Phylogenetic Visualization", Last Revised Oct. 11, 1996.*

* cited by examiner

*Primary Examiner*—Hwa C. Lee
(74) *Attorney, Agent, or Firm*—Reed Smith LLP; Stanley P. Fisher, Esq.; Juan Carlos A. Marquez, Esq.

(57) ABSTRACT

A method of comparing dendrograms created by different references or algorithms displays individual dendrograms (201, 202) on a screen in an overlapped yet distinguishable manner. The overlapped portions of the dendrograms are displaced vertically or horizontally from one another and indicated by different colors for individual dendrograms. A specified branch and elements hanging therefrom can be highlighted when displayed, such that differences in the manner in which individual elements of the overlapped dendrograms are clustered can be easily recognized.

7 Claims, 13 Drawing Sheets

FIG.5

| | |
|---|---|
| DENDROGRAM OVERLAP INFORMATION TABLE | 501 |
| DENDROGRAM ID I | 502 |
| DENDROGRAM ID II | 503 |
| LINE TYPE INFORMATION I | 504 |
| LINE TYPE INFORMATION II | 505 |
| REFERENCE DENDROGRAM ID | 506 |
| STANDARDIZATION METHOD INFORMATION | 507 |

DENDROGRAM DISPLAYING METHOD

This application claims priority to Japanese application serial No. 172922/2001, filed Jun. 7, 2001.

BACKGROUND OF THE INVENTION

1. Technical Field

The present invention relates to a method of displaying a dendrogram, and more particularly to a method of displaying a plurality of dendrograms created from the same group of elements in a comparable manner.

2. Background Art

Recent years have witnessed progress in experiment methods in molecular biology. It is now possible to quickly collect biopolymer data on genetic sequences, for example. Such data can be digitized or converted into numerical terms according to a single reference or algorithm and then processed by a computer to provide quantified relationships among biomolecules, which can be displayed in the form of a dendrogram.

The quantified relationships among elements in a group of elements based on a single reference or algorithm can be easily displayed in the form of a dendrogram. There are cases where it is desired to quantify relationships among elements in the same group of elements based on different references or algorithms, so that the resultant, individual dendrograms can be compared. A typical example of the reference for comparison of dendrograms is clustering or the manner in which individual elements are clustered. In a dendrogram, a change in the order of the elements displayed can cause its topology to be changed without disturbing numerical relationships. Thus, it is extremely difficult to simply compare dendrograms indicating the inter-element relationships in the same group of elements.

It is therefore a first object of the present invention to provide a display method which can clarify differences in dendrograms that are created by quantifying elements in the same group of elements based on different references or algorithms. It is a second object of the present invention to provide a display method by which differences in the manner in which individual elements are clustered in dendrograms can be easily judged.

SUMMARY OF THE INVENTION

In accordance with the present invention, individual dendrograms are displayed on a single screen in an overlapped yet distinguishable manner, in which (1) overlapped portions of the dendrograms are displaced vertically or horizontally from one another, and (2) the individual dendrograms are indicated by different display colors or types of line. Further, (3) in an overlap dendrogram that is displayed, specified branches in a certain dendrogram and elements that hang from those branches are highlighted, wherein (4) the elements are rearranged such that specified branches do not cross one another. Further, (5) the dendrograms are displaced visually vertically or horizontally such that overlapped branches do not wrap over one another in dendrograms other than a specified dendrogram. As a display option, (6) the distances between root node and terminals are made uniform, or (7) the distances between nodes of each branch are made uniform. Further, (8) the shapes of branches in a dendrogram may be modified or stored starting from a node of an arbitrary branch. By the display methods (1) and (2), individual dendrograms can be displayed on a single screen in an overlapped, yet distinguishable manner. By the display methods (3) to (8), the dendrograms can be displayed in an overlapped manner such that differences in the way the elements are clustered between the overlapped dendrograms can be easily recognized.

Specifically, the present invention provides a method of displaying a dendrogram which expresses quantified relations among elements in a group of elements, the method comprising the steps of creating a plurality of types of dendrograms based on the same group of elements by different inter-element quantification methods and/or different dendrogram creation methods, selecting one of the plurality of types of dendrograms as a reference dendrogram, converting another dendrogram such that the order of its elements is the same as that of the reference dendrogram, and displaying the reference dendrogram and the another, converted dendrogram in an overlapped manner.

The plurality of types of dendrograms may map expression profiles of genes as elements according to a plurality of clustering algorithms. Further, the plurality of types of dendrograms may map the result of phylogenetic analysis of different genes of animal species as elements.

BRIEF DESCRIPTION OF THE DRAWINGS

The present invention will be hereafter described in detail by way of embodiments with reference made to the drawings in which:

FIG. 5 shows an example of a dendrogram overlap information data structure for retaining dendrogram overlap information;

DETAILED DESCRIPTION OF PREFERRED EMBODIMENTS

Figure 1:
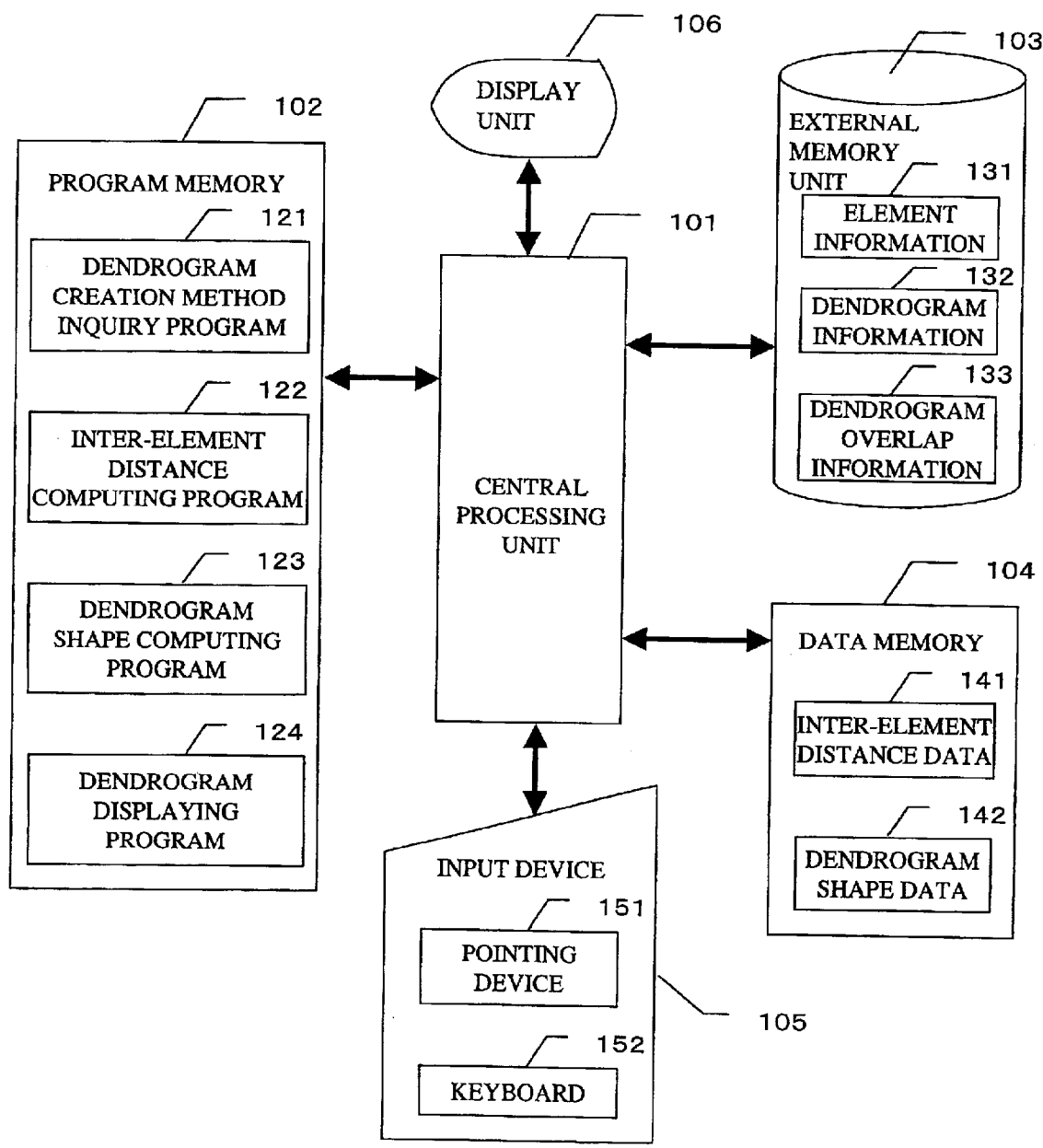
FIG. 1 shows a diagram of an overlap dendrogram display system according to the present invention.

FIG. 1 shows a diagram of the system configuration of a dendrogram display system according to the present invention. The dendrogram display system comprises a central processing unit 101 for performing computations for the correction of measurement errors between two samples and data processing for displaying a dendrogram, a program memory 102 in which programs to be run by the central processing unit 101 for performing processes are stored, an external storage unit 103 such as, e.g., a hard disc, a data memory 104 for the temporary storage of data, an input device 105 for inputting values into the system or selecting values, and a display unit 106 for visually displaying dendrogram data and thus providing interaction with the user.

In the program memory 102, there are stored programs such as, e.g., a dendrogram creation method inquiry program 121 for inquiring the user about element data, a quantification method, and a dendrogram creation algorithm for the creation of a dendrogram, an inter-element distance computing program 122 for quantifying the element data specified by the user according to a designated quantification method, a dendrogram-shape computing program 123 for creating a dendrogram based on quantified inter-element distance data according to the user-specified dendrogram creation algorithm, and a dendrogram display program 124 for displaying created dendrograms in an overlapped manner. These programs may be provided as recorded on a recording medium such as, e.g., a floppy disc, CD-ROM, DVD-ROM, or MO. They may also be provided via networks.

In the external storage unit 103, there are stored element information 131 about biopolymer presence amount data where the degree of presence of biopolymers in a sample is stored in numerical terms, dendrogram information 132 where information about dendrograms with different computations and shapes are stored, and dendrogram overlap information 133 where information for displaying dendrograms in an overlapped manner is stored. In the data memory 104, there are stored inter-element distance data 141 for retaining the results of computation of individual elements of biopolymers, and dendrogram-shape data 142 for retaining dendrogram shapes and overlap information computed from inter-element distances. The input device 105 comprises a pointing device 151 and a keyboard 152, for example.

Figure 2:
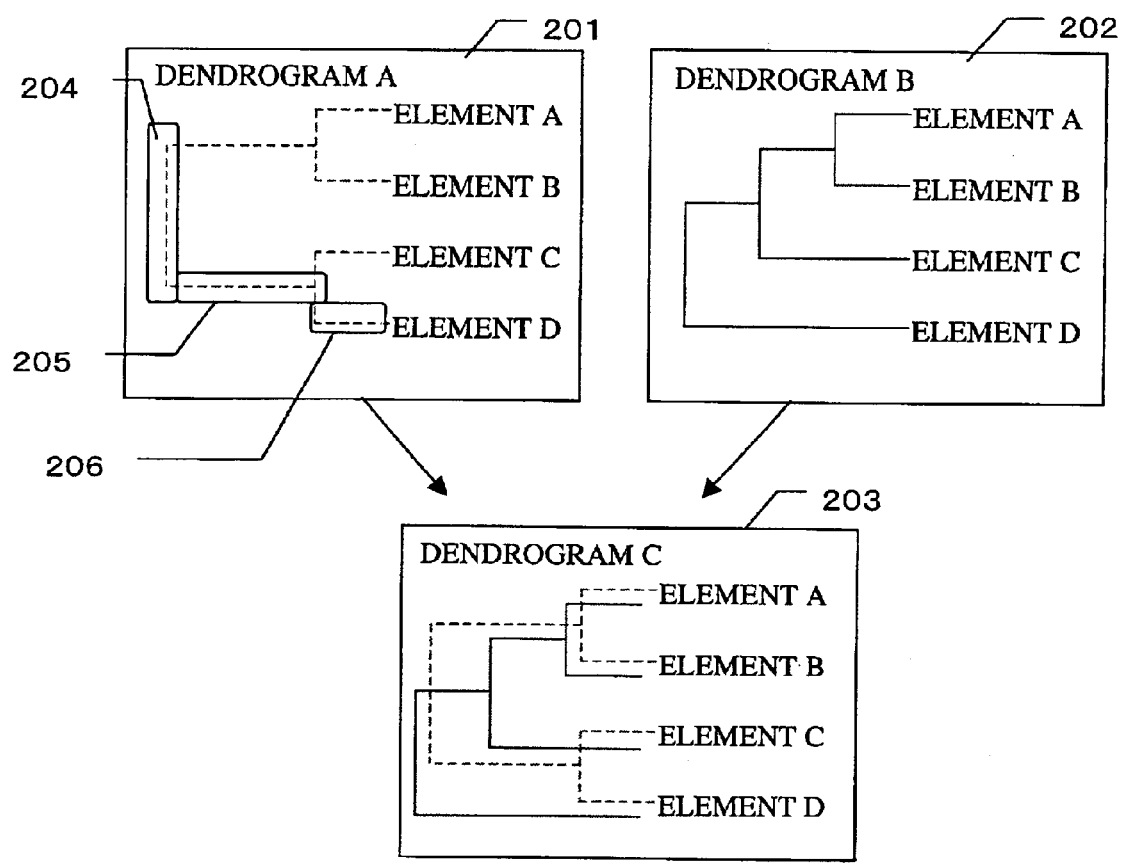
FIG. 2 illustrates the basic concept of an overlap dendrogram which is created on the basis of two dendrograms.

FIG. 2 illustrates the basic concept of the overlap dendrogram provided by the present invention. The central processing unit 101 of FIG. 1 processes data about a certain group of elements (element A, element B, element C, element D) according to a certain inter-element distance computation reference or a dendrogram-shape computation algorithm, thereby to create a dendrogram A 201 representing inter-element relationships. Further, the same element group data is processed according to a different inter-element distance computation reference or dendrogram creation algorithm to create a dendrogram B 202 representing inter-element relationships. Of these individual dendrograms, one (such as dendrogram B 202 in the illustrated example) is used as a reference, while the other dendrogram A 201 is converted such that the order of its elements is the same as that of the dendrogram B 202. The dendrograms are then processed by the central processing unit 101 of FIG. 1 to displace the overlapped portions of the displayed dendrograms vertically or horizontally, or to display the individual dendrograms with different types of lines or colors, so that there is displayed on the display unit 106 a dendrogram C 203 which shows the individual dendrograms in a distinguishable manner. In the dendrograms, a branching-out portion such as a part 204 is called a node, a portion connecting one node to another, such as a part 205, is called a branch, and a portion serving as a terminal end of the dendrogram, such as a part 206, is called a leaf.

Figure 3:
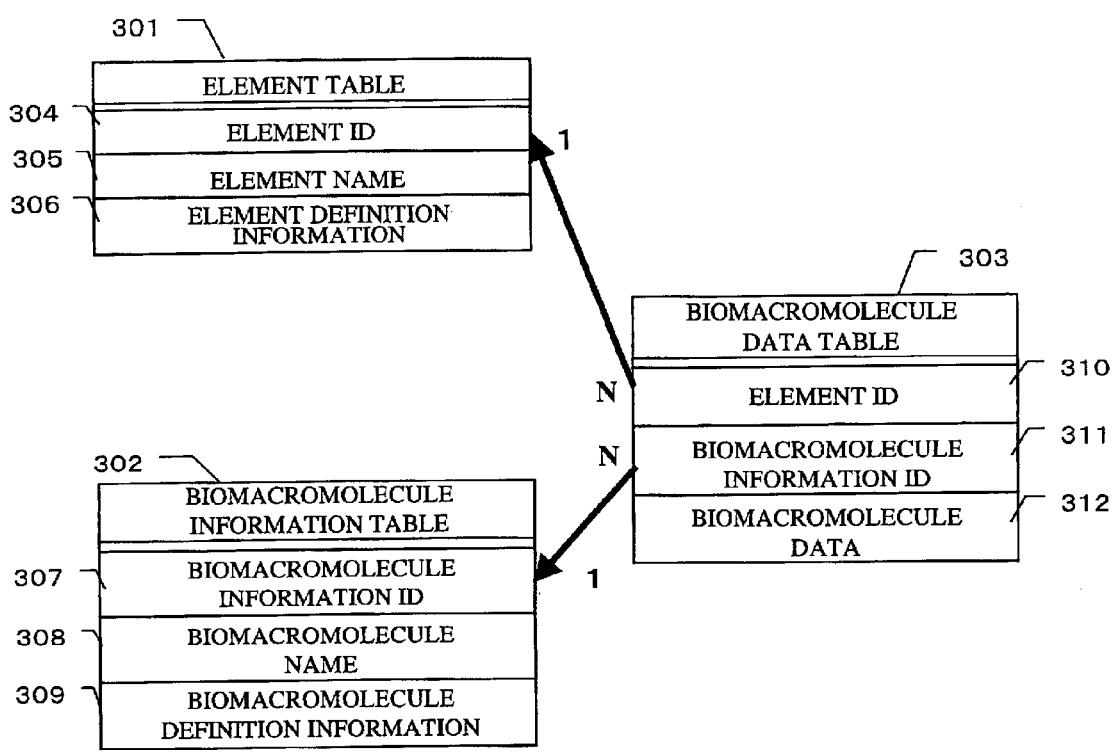
FIG. 3 shows an example of a biopolymer data structure for retaining elements, biopolymer information, and biopolymer data from which a dendrogram is created.

FIG. 3 shows an example of the data structure of the element information. The element information 131 comprises an element table 301, a biopolymer information table 302, and a biopolymer data table 303. The element table 301 has individual fields for an element ID 304 for storing an ID for uniquely identifying each element, an element name 305 for storing element names, and an element definition information 306 for storing information relating to elements. The biopolymer information table 302 has individual fields for a biopolymer information ID 307 for storing an ID for uniquely identifying each biopolymer, a biopolymer name 308 for storing biopolymer names, and biopolymer definition information 309 for storing the definition of each biopolymer. The biopolymer data table 303 has individual fields for an element ID 310 for storing an ID specifying data of an element in the element table 301, a biopolymer information ID 311 for storing an ID specifying biopolymer information in the biopolymer information table 302, and biopolymer data 312 for storing the biopolymer data of an element uniquely identified by the element ID and by the biopolymer information ID. For example, by storing the genus and species name of a bacterium in the element table 301, a 16S rDNA sequence of the bacterium in the biopolymer information table 302 as the biopolymer name, and 16S rDNA sequence of the genus and species identified by the element ID in the biopolymer data table, there can be obtained elements for creating a dendrogram according to the 16S rDNA sequence of the bacterium.

Figure 4:
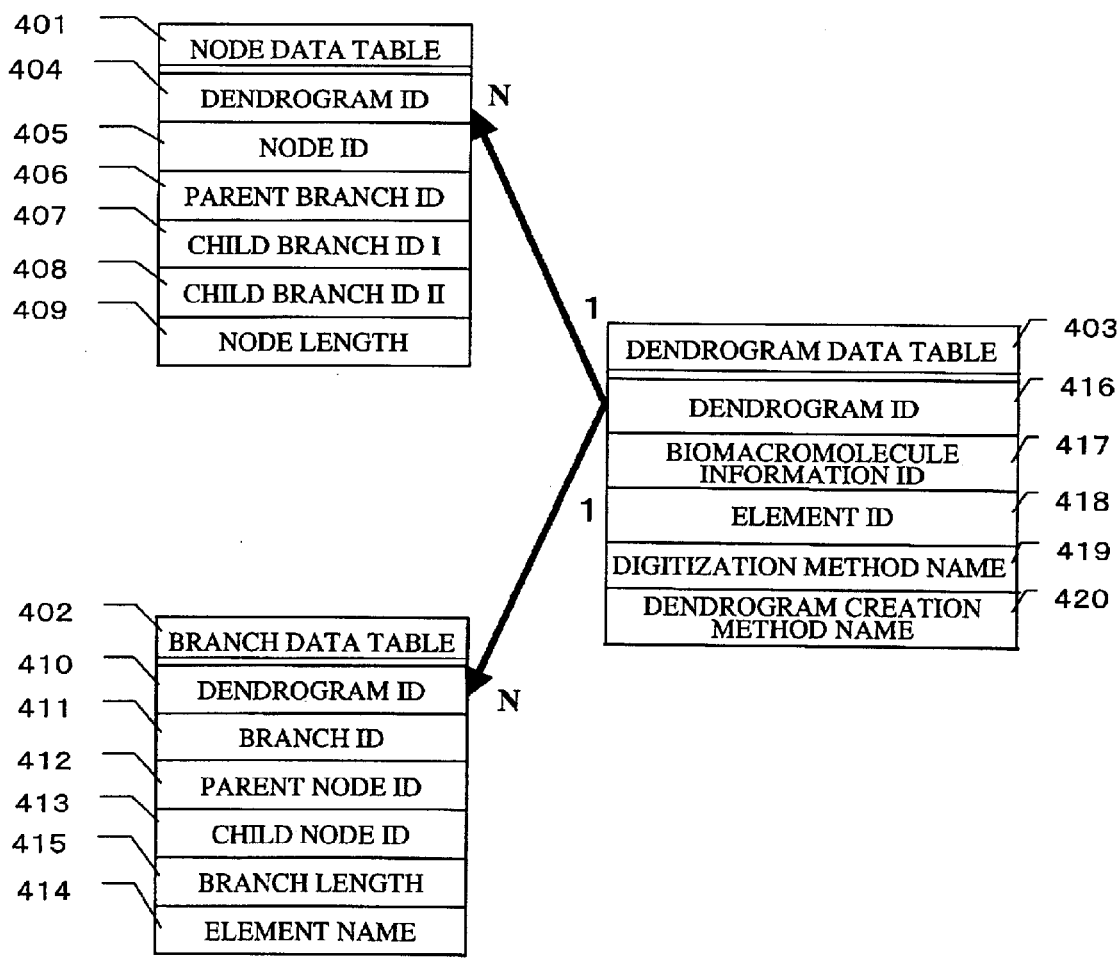
FIG. 4 shows an example of a dendrogram data structure for retaining node data, branch data, and dendrogram data for a dendrogram.

FIG. 4 shows an example of the data structure of the dendrogram information. The dendrogram information 132 comprises a node data table 401 having information about individual nodes, a branch data table 402 having information about branches or leaves, and a dendrogram data table 403 having data about the dendrogram itself. The node data table 401 has individual fields for a dendrogram ID 404 for identifying which dendrogram the data pertains to, a node ID 405 for uniquely identifying the node itself, a parent branch ID 406 for uniquely identifying a branch that is to become a parent, a child branch ID I 407 and a child branch ID II 408 for uniquely recognizing branches that are to become child branches, and a node length 409 for retaining information about the length of the node. The branch data table 402 has individual fields for a dendrogram ID 410 for identifying which dendrogram the data belongs to, a branch ID 411 for uniquely identifying the branch itself, a parent node ID 412 for uniquely identifying a node that is to become a parent, a child node ID 413 for uniquely identifying a node that is to become a child, a branch length 414 for retaining information about the length of the branch, and an element name 415 for retaining an element name in the case where there is no child node but there is a leaf. The dendrogram data table 403 has individual fields for a dendrogram ID 416 for uniquely identifying the dendrogram itself, a biopolymer information ID 417 for uniquely identifying biopolymer information that are expressed in the form of a dendrogram, an element ID 418 for uniquely identifying elements that are expressed in the form of a dendrogram, a digitization method name 419 for retaining a digitization method name, and a dendrogram creation method name 420 for retaining the name of the dendrogram creation method used for the creation of a dendrogram based on inter-element distances. If there is not the parent ID 406 in the node data table 401, the node is a root node, and if there is not the child node ID 413 in the branch data table 402, there is a leaf. Because there is the node length field 409 in the node data table 401, and by aligning the order of the child branches 1 and 2 with the order in the dendrogram, the shape of the dendrogram can also be retained.

FIG. 5 shows an example of the data structure of the dendrogram overlap information. Dendrogram overlap information 133 is stored in a dendrogram overlap information table 501. The dendrogram overlap information table 501 has individual fields for a dendrogram ID I 502 for uniquely identifying dendrograms to be displayed in an overlapped manner, a dendrogram ID II 503, line type information I 504 for retaining the shape and color of the lines used in drawing the dendrogram according to the dendrogram ID I, line type information II 505, a reference dendrogram ID 506 for uniquely identifying a dendrogram to be used as a reference during an overlapped display, and a standardization method information 507 for retaining information about the standardization method used in an overlapped display.

Figure 6:
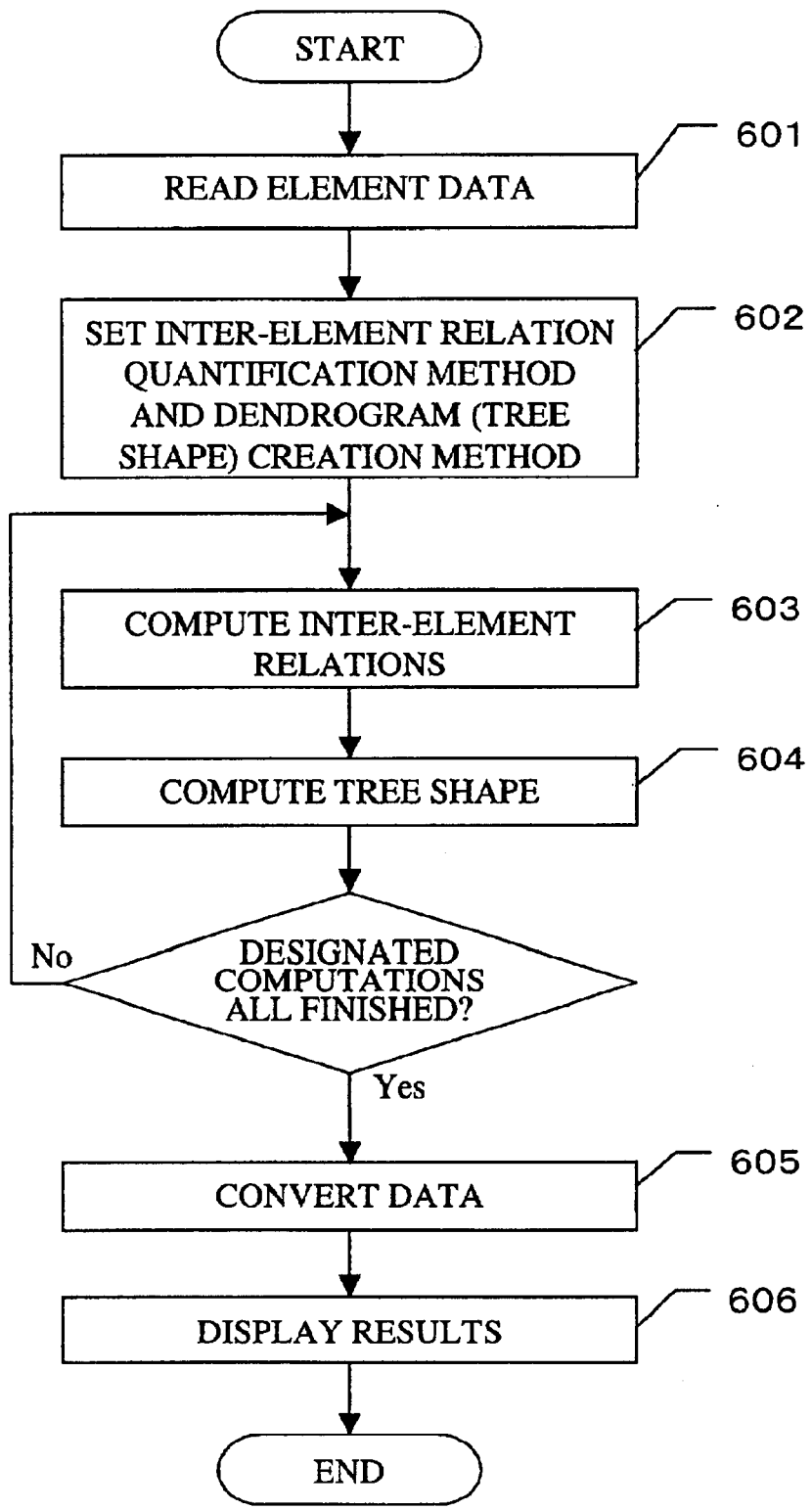
FIG. 6 shows a flowchart of the process from the reading of elements to the display of an overlap dendrogram.

FIG. 6 shows a processing flow for displaying in the display unit 106 of FIG. 1 an overlapped dendrogram based on the biopolymer presence amount data stored in the element information 131 of FIG. 1. As the process starts, element data is read (step 601), whereby data about the amount of biopolymers present in each element of a group of elements is read from the element information 131 into the central processing unit 101 of FIG. 1. Next, the inter-element relation quantification method and the dendrogram creation method are set (step 602). In this step, the user is inquired through the display unit 106 about the inter-element relation quantification method (for digitizing the element data and quantifying the relationships among digitized element data) and the dendrogram creation method (for creating a dendrogram based on the relationships among the digitized element data) that are used when a dendrogram is created by the central processing unit 101 based on the data about individual elements read by the element data reading step. The user is further asked to set these methods using the pointing device 151 or the keyboard 152. During this step, the central processing unit runs the dendrogram creation method inquiry program 121.

Thereafter, inter-element relationship computation is performed (step 603), where the data read in the element data reading step 601 are digitized and the inter-element relationships are quantified according to the methods set in step 602, i.e., the inter-element relation quantification method and the dendrogram creation method, with the central processing unit 101 running the inter-element distance computation program 122. This is followed by a dendrogram-shape computation step (step 604), in which dendrogram data is generated according to the dendrogram creation method that was set in step 602, where the inter-element relation quantification method and dendrogram creation method were set, with the central processing unit 101 running the dendrogram-shape computation program 123. The dendrogram A 201 shown in FIG. 2 is an example of the dendrogram obtained in this step.

Thereafter, the inter-element relation computation in step 603 and the dendrogram-shape computation in step 604 are repeated with regard to the same element group as that read by the element data reading step 601, while using different quantification and dendrogram creation methods than those specified by the setting of the inter-element relation quantification method and dendrogram creation method in step 602. As a result, there is obtained a dendrogram computed by a different inter-element relation quantification and dendrogram creation method based on the same element group, the dendrogram having a different topology. The dendrogram B 202 shown in FIG. 2 is an example of the dendrogram obtained in this step.

Then, data conversion is performed (step 605), in which the dendrogram display program 124 is run by the central processing unit 101, and data on a plurality of dendrograms obtained by the dendrogram-shape computation in step 604, such as the dendrogram A 201 and dendrogram B 202 shown in FIG. 2, are converted into a dendrogram in an overlapped display mode, such as the dendrogram C 203 shown in FIG. 2. The result of conversion is then displayed (step 606), in which the overlap dendrogram obtained by the data conversion in step 605 is displayed on the display unit 106.

Figure 7:
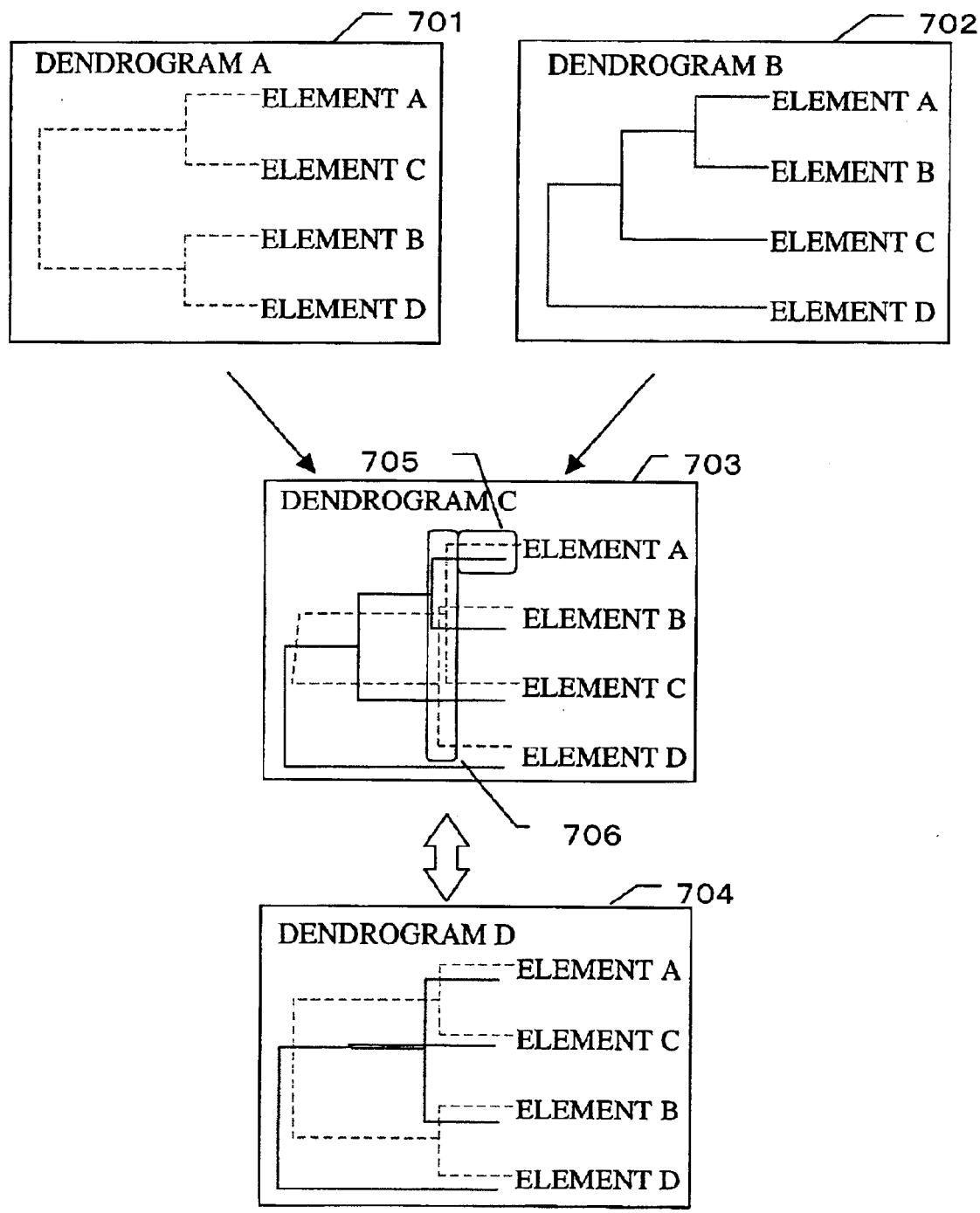
FIG. 7 illustrates the manner in which the order of elements in an overlap dendrogram is changed based on the order of elements in a specified dendrogram.

FIG. 7 shows an example of display of a dendrogram in which the order of display (order of elements) is specified. A dendrogram A 701 and a dendrogram B 702 are created by the central processing unit 101 based on the group of elements A, B, C, and D according to the flow of FIG. 6. The central processing unit 101 converts the data in the data conversion step 605 of FIG. 6, such that the order of elements in the dendrogram A 701 corresponds to the order of elements in the dendrogram B 702. In the result display step 606 of FIG. 6, an overlap dendrogram C 703 is displayed on the display unit 106 in which the element order of the dendrogram A 701 is converted on the basis of the element order of the dendrogram B 702.

The dendrogram C 703 is displayed in an overlapped manner such that individual branches of the dendrograms A and B do not overlap one another (portion 705). The branches of the dendrogram A 701 that does not serve as a reference for the element order are visually displaced horizontally or vertically (portion 706) such that individual branches do not overlap one another. When the user changes the reference to the dendrogram A 701 by means of the pointing device 151 or keyboard 152, the dendrogram C 703 is computed again by the central processing unit 101, whereby a dendrogram D 704 is displayed in which the element order of the dendrogram B 702 is aligned with that of the dendrogram A. When the dendrogram D 704 is created, computations are performed to displace branches horizontally or vertically, such that the branches of the dendrogram A 702, which is not the basis of the element order, do not overlap when displayed. In the thus created dendrogram D 704, if the user once again changes the reference to the dendrogram A 702, the dendrogram D 704 is re-computed so that the dendrogram C 703 is displayed which corresponds to the element order of the dendrogram A 702.

Figure 8:
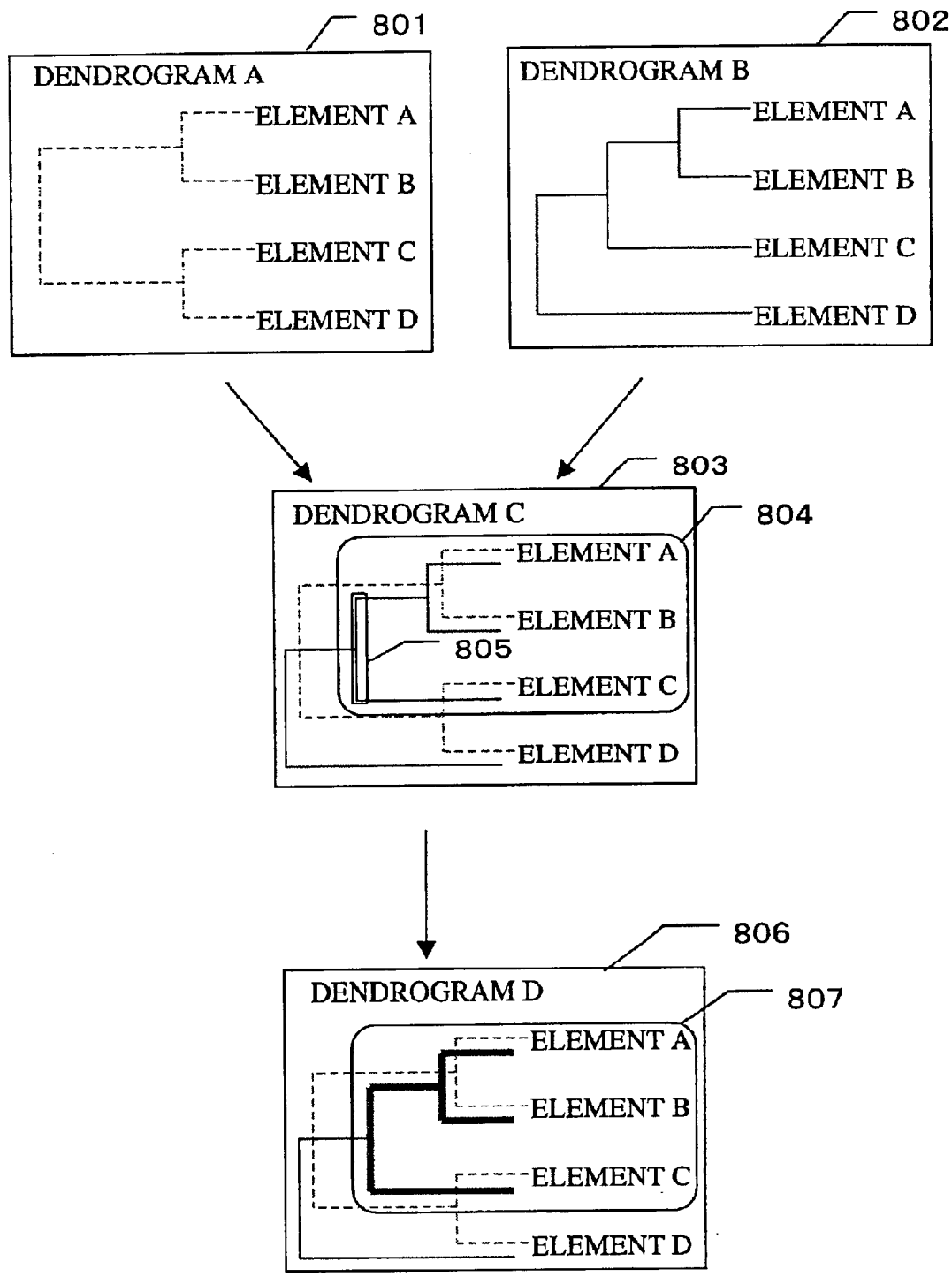
FIG. 8 illustrates the manner in which a specified branch and a group of elements hanging from that branch are highlighted in an overlap dendrogram.

FIG. 8 shows an example of display of an overlap dendrogram in which a specified branch and elements hanging therefrom are highlighted. According to the flow of FIG. 6, in the case where there are a dendrogram A 801 and a dendrogram B 802 that have been created from a group of elements A, B, C, and D, as well as a dendrogram C 803 computed from these two dendrograms and displayed on the display unit 106, if the user specifies a branch 805 in the dendrogram C 803 by means of the pointing device 151 or keyboard 152, the specified branch 805 and elements 804 (including branches and element names) hanging therefrom are re-computed by the central processing unit 101 and displayed in the dendrogram D 806 as highlighted elements (including branches and the element names).

Figure 9:
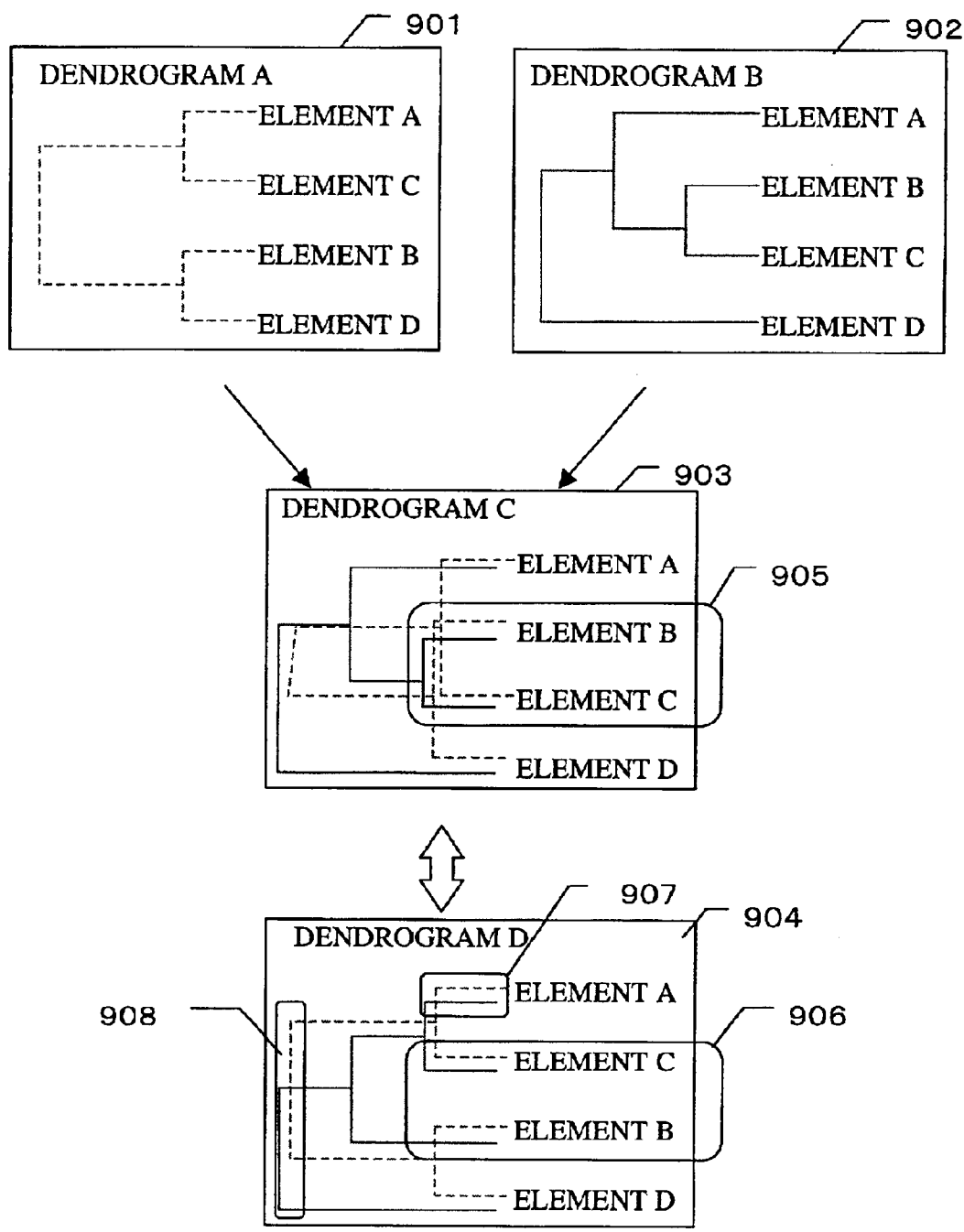
FIG. 9 illustrates the manner in which the order of elements of a specified branch is changed in an overlap dendrogram.

FIG. 9 illustrates the processing performed when the element order in an overlap dendrogram is changed. In the case where an overlap dendrogram C 903 has been created from two dendrograms A 901 and B 902 based on the same element group, with the dendrogram B 902 used as the element order, if the user demands a change in the order by specifying a partial element group 905 formed by elements A and B of the dendrogram B, the central processing unit 101 performs re-computations so that the dendrogram C 903 is converted into a dendrogram D 904. The partial dendrogram structure 905 comprising the elements A and B that had been specified prior to write-over is converted into a partial dendrogram structure 906 in which the order of the elements A and B is reversed. The dendrogram structure converted from the dendrogram A 901 that was not specified during this conversion is displaced vertically (portion 907) or horizontally (portion 908) when displayed such that the individual branches of the dendrograms B and A do not overlap one another. In this way, the branches originating from the dendrogram A, such as a portion 906 with respect to the portion 905 of the dendrogram C, can be displayed in a manner that is more easily recognizable. The user can perform a storage operation on the overlap dendrogram D 904 in which the element order has been changed in order to store information about the individual dendrograms in the dendrogram information 132 and information about the overlap dendrogram in the dendrogram overlap information 133, with the element order changed.

Figure 10:
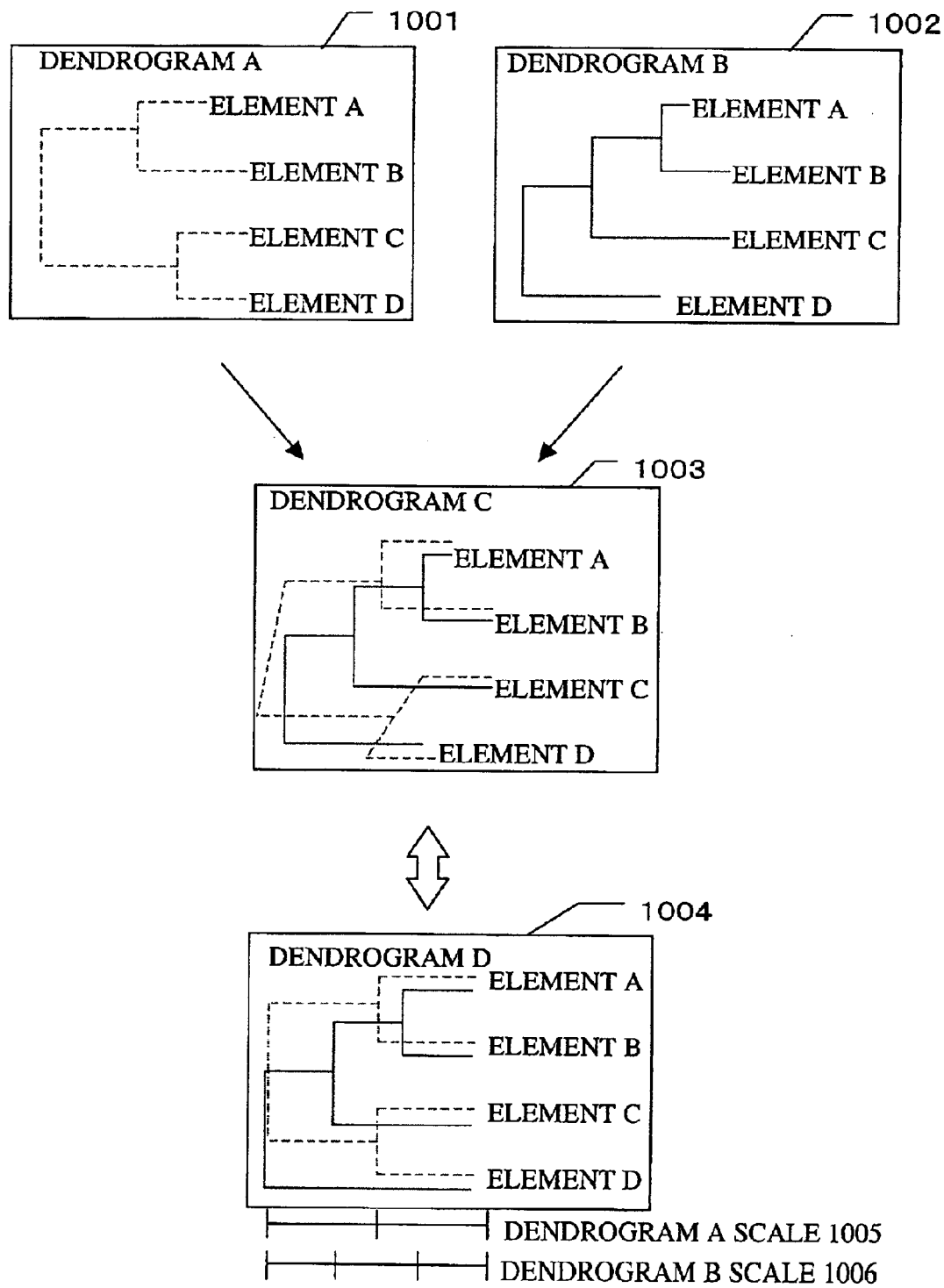
FIG. 10 illustrates the manner in which dendrograms to be overlapped are standardized whereby the distances between root node and terminals are made uniform.

FIG. 10 illustrates a standardization processing performed on the dendrogram. In the case where an overlap dendrogram C 1003 has been created from dendrograms A 1001 and B 1002 based on the same element group, with the dendrogram B 1002 serving as a reference, the lengths of branches in the dendrogram A are converted such that they can be displayed over the dendrogram B in an overlapped manner with the angles of the branches varied. At this time, if the user demands standardization of the dendrogram by means of the pointing device 151 or keyboard 152, the overlap dendrogram C 1003 is converted into an overlap dendrogram D 1004 in which the distances between root node and terminal elements are unified. During the conversion, the length of a branch from a node to a terminal end is converted into the length which is obtained by first equally dividing the length between the root and the terminal end by a maximum number of nodes in the elements in a dendrogram, and then multiplying one equal part by a value obtained by subtracting from the maximum number of nodes the number of branching-off of each element or cluster (partial element group) from the root.

For example, each branch in the dendrogram A has a maximum node number of 2 from the root, and the number of branching-off at each node is one. Accordingly, the length of the branches beyond the node is equally divided into the lengths shown in a scale 1005 for the dendrogram A. In the case of elements A and B of the branches in the dendrogram B, the maximum number of nodes is three while the number of branching-off is two. Therefore, the length between the root and the terminal end is equally divided in three, and a ⅓ part is multiplied by 3−2=1 to give the length equal to one division of a scale 1006 for the dendrogram B. With regard to the partial element group of the elements A and B and the element C, the maximum number of nodes is three while the number of branching-off is one. Therefore, the distance between the root and the terminal end is equally divided in three and a ⅓ part is multiplied by 3−1=2 to give a length equal to two thirds of the equal parts, which is equal to two divisions of the scale 1006 for the dendrogram B. With regard to the element D and the partial element group comprising the elements A, B, and C, the maximum number of nodes is three and the number of branching-off is zero, so that the length of the branch is equal to three divisions of the scale 1006 for the dendrogram B which is obtained by multiplying a ⅓ part of the length between the root and the terminal end with 3−0=3. When the overlap dendrogram D 1004 after standardization is displayed, if the user demands cancellation of the standardization of the dendrogram, the dendrogram D is converted into the dendrogram C which reflects the lengths of the individual branches.

Figure 11:
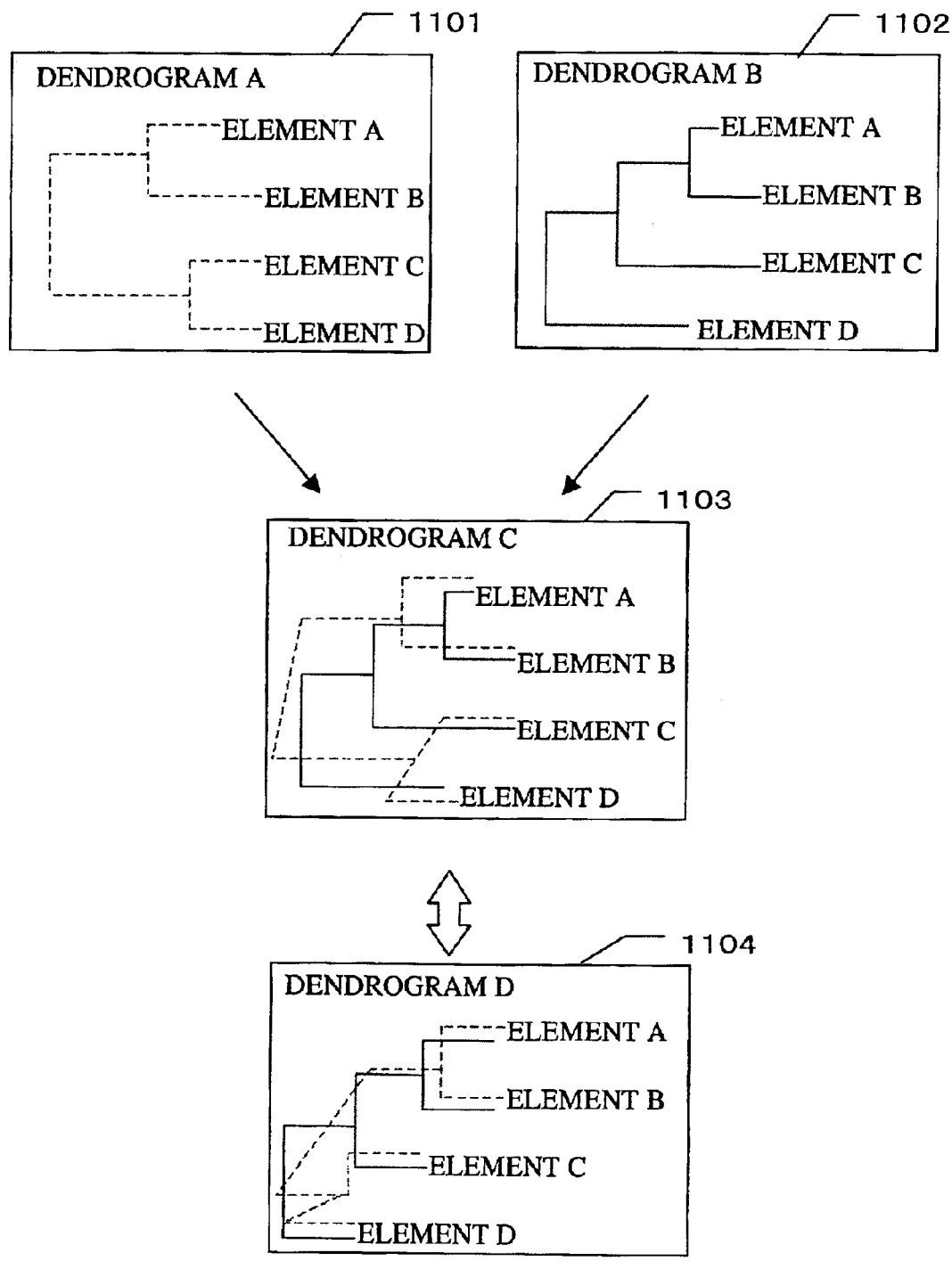
FIG. 11 illustrates the manner in which the distances between nodes of each branch are made uniform.

FIG. 11 illustrates a branch standardization process. In the case where an overlap dendrogram C 1103 has been created from a dendrogram A 1101 and a dendrogram B 1102 based on the same element group, with the dendrogram B 1102 as a reference, the lengths of the branches in the dendrogram A are converted so that the dendrogram A can be displayed over the dendrogram B in an overlapped manner with the angles of the branches varied. If the user demands standardization of the branches by using the pointing device 151 or keyboard 152, the overlap dendrogram C 1103 is converted into an overlap dendrogram D 1104 where the distances of individual branches between nodes are unified. During conversion, the length of a branch between one node to the next node or a terminal element is equal to a length which is obtained by dividing the distance between the root to the terminal end by a maximum number of nodes of elements in the dendrogram B. The branches of the dendrogram A in the overlap dendrogram D 1104 created on the basis of the element order of the dendrogram B are displayed in the order of the dendrogram B.

Figure 12:
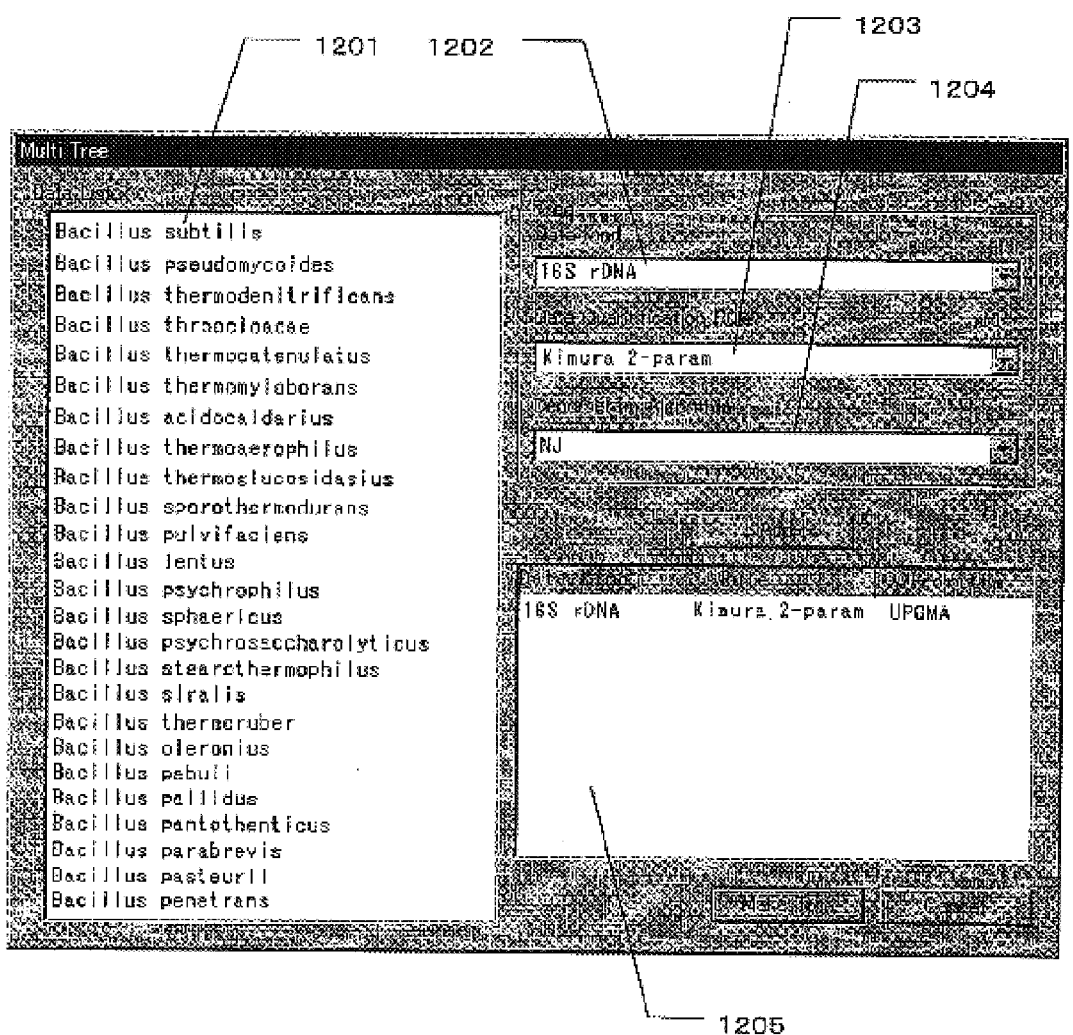
FIG. 12 shows an example of a user interface for specifying source data, the inter-element relation quantification method, and the dendrogram creation algorithm for the creation of a dendrogram.

FIG. 12 shows a user interface for inquiring the user about the methods for inter-element relation quantification and dendrogram creation in step 602 of the processing flow shown in FIG. 6 where the inter-element relation quantification method and the dendrogram creation method are set.

Items that are displayed include a data list 1201 indicating a group of individual elements for which relations are to be displayed, a data type box 1202 for the types of data possessed by each element for quantification, an inter-element relation quantification method box 1203 for the selection of a method for quantifying the distance between element macromolecule data, a relation-expressing dendrogram creation algorithm box 1204 for specifying the method of creating a dendrogram expressing relations based on quantified inter-element distances, and a list 1205 listing the data type, relation quantification methods, and the dendrogram-creation algorithm conditions for creating individual dendrograms. The user specifies the data type of the group of elements shown in the data list 1201, the relation quantifying method, and the dendrogram creation algorithm via this interface.

The elements may be genes, the data type may be an expression pattern, the inter-element distance may be Euclidean distance (Kinji Mizuno: Tahenryo Dehta Kaiseki Kohgi ("Lectures on Multivariate Data Analysis"). Asakura Shoten, 1996), the relation-expressing dendrogram creation algorithm may be Ward's method (Kinji Mizuno: Tahenryo Dehta Kaiseki Kohgi ("Lectures on Multivariate Data Analysis"), or the nearest neighbor method (Kinji Mizuno: Tahenryo Dehta Kaiseki Kohgi ("Lectures on Multivariate Data Analysis"), so that results of gene cluster analysis can be compared. Further, the elements may be animal species, the data type may be a genetic sequence, the inter-element distance is evolution distance according to Kimura's 2-parameter model (Kimura, M.: A sample method for estimating evolutionary rates of base substitutions through comparative studies of nucleotide sequences. J. Mol. Evol. 16, pp.291–296, 1980), and the relation-expressing dendrogram creation algorithm may be the NJ method (Saito, N. and Nei, M.: The neighbor-joining method for reconstructing phylogenetic trees. Mol. Bio. Env. 4, pp.406–425, 1987), or the UPGMA method (Tateno: Bunshi-keitohju no tsukurikata to sono-hyoka ("Method of Creating a Molecule Dendrogram and Its Evaluation"). Kimura (ed): Bunshi-shinkagaku-nyumon ("Introduction to Molecular Evolution"). Baifukan, 1984), so that results of phylogenetic analysis of genes of animal species can be compared.

Figure 13:
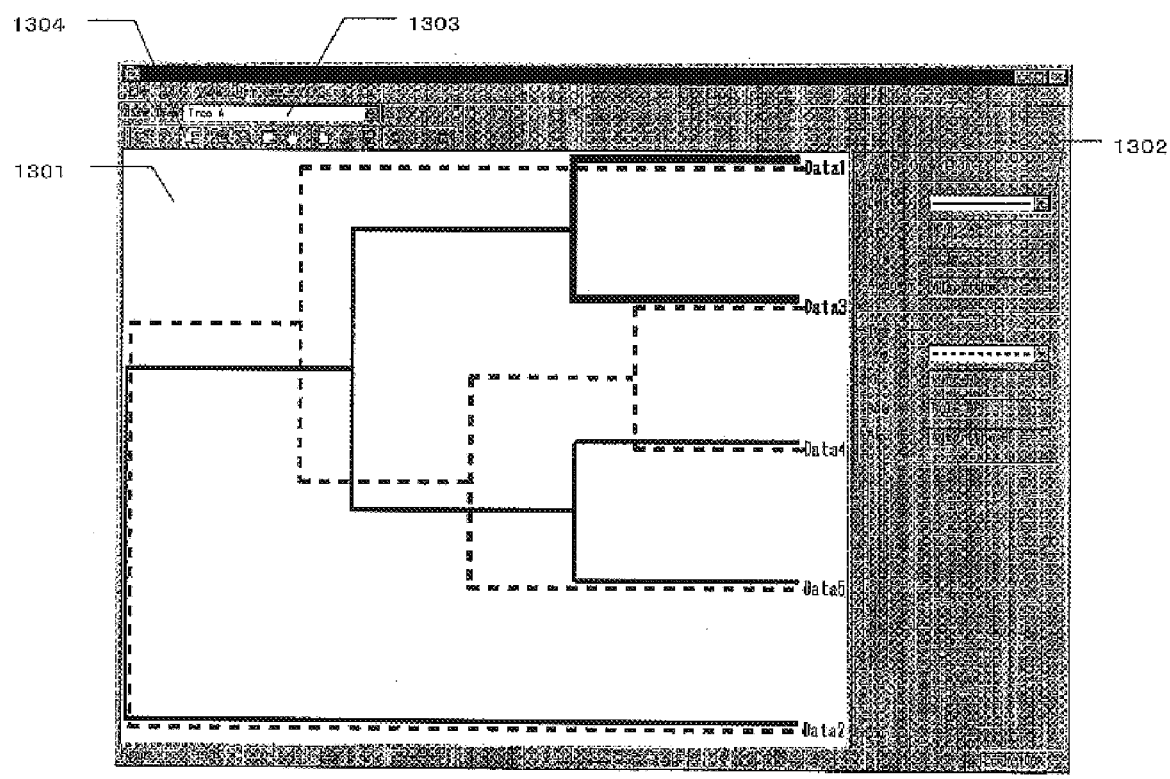
FIG. 13 shows an example of a user interface for displaying a created dendrogram.

FIG. 13 shows a user interface for the display of an overlap dendrogram. Items that are displayed include a dendrogram window 1301 where dendrograms are displayed in an overlapped manner, a dendrogram information window 1302 where the display colors of the individual dendrograms, the type of data, the relation quantification method, and the dendrogram creation algorithm are listed, a reference dendrogram box 1303 where a drawing reference dendrogram is indicated, and a button 1304 for performing various operations on the overlap dendrogram (including highlighting a specified branch, changing the element order, standardization of the dendrogram or branches, selection of display sizes such as enlarged, reduced or original, and creation, storage or read-in of an overlap dendrogram).

Thus, in accordance with the present invention, different types of dendrograms, in which quantified inter-element relations are expressed, are created based on a certain group of elements according to different methods of quantification of inter-element relations and creation of a dendrogram. The different types of dendrograms can be displayed in an overlapped manner on a single screen. Accordingly, the present invention allows element clustering differences caused by the difference in the inter-element relation quantification method and dendrogram creation method to be displayed in a comparable manner.

What is claimed is:

1. A method of displaying a dendrogram representing quantified relations among elements of a group of elements, the method comprising the steps of:

creating a plurality of types of dendrograms based on the same group of elements according to different inter-element relation quantification methods and/or different dendrogram creation methods;

selecting one of the plurality of types of dendrograms as a reference dendrogram;

converting another dendrogram such that the order of its elements is the same as that of the reference dendrogram; and displaying the reference dendrogram and the converted dendrogram in an overlapped manner by aligning a direction from branches to leaves of the reference dendrogram and that of the converted dendrogram in parallel and with an identical orientation thereby sharing the elements, wherein nodes, branches and leaves of the plurality of types of dendrograms that are displayed do not overlap one another, and the order of elements of a branch in a selected dendrograms can be changed starting from a specified node.

2. A method of displaying a dendrogram according to claim 1, wherein the individual dendrograms are displayed by different colors and/or types of lines.

3. A method of displaying a dendrogram according to claim 1, wherein a specified branch or node of a selected dendrogram, and a branch, node and element hanging from the specified branch or node are highlighted when displayed.

4. A method of displaying a dendrogram according to claim 1, wherein the dendrograms are standardized such that the distances between a root node and a terminal element of each of the plurality of types of dendrograms that are displayed in an overlapped manner are unified, or the branches are standardized such that the distances between nodes of individual branches are unified.

5. A method of displaying a dendrogram according to claim 1, wherein the plurality of types of dendrograms are created by using a plurality of clustering algorithms, the dendrograms mapping expression profiles of genes as elements.

6. A method of displaying a dendrogram according to claim 1, wherein the plurality of types of dendrograms show the results of phylogenetic analysis of genes possessed by individual animal species as elements according to different relation quantification methods and/or different dendrogram creation methods.

7. A computer-executed program of a method of creating a dendrogram, the method comprising the steps of:

creating a plurality of types of dendrograms based on the same group of elements according to different inter-element relation quantification methods and/or different dendrogram creation methods;

selecting one of the plurality of types of dendrograms as a reference dendrogram;

converting another dendrogram such that the order of its elements is the same as that of the reference dendrogram; and displaying the reference dendrogram and the converted dendrogram in an overlapped manner by aligning a direction from branches to leaves of the reference dendrogram and that of the converted dendrogram in parallel and with an identical orientation thereby sharing the elements, wherein nodes, branches and leaves of the plurality of types of dendrograms that are displayed do not overlap one another, and the order of elements of a branch in a selected dendrograms can be changed starting from a specified node.

* * * * *